United States Patent [19]

Citron

[11] Patent Number: 5,135,467
[45] Date of Patent: Aug. 4, 1992

[54] IMPLANTABLE SYSTEM AND METHOD FOR CORONARY PERFUSIONS ASSISTANCE

[75] Inventor: Paul Citron, New Brighton, Minn.

[73] Assignee: Medtronic, Inc., Minneapolis, Minn.

[21] Appl. No.: 447,493

[22] Filed: Dec. 7, 1989

[51] Int. Cl.$^5$ ............................................. A61M 1/12
[52] U.S. Cl. ...................................................... 600/16
[58] Field of Search ............ 128/419 R, 421; 600/16, 600/17, 18

[56] References Cited

U.S. PATENT DOCUMENTS

| | | | |
|---|---|---|---|
| 4,411,268 | 10/1983 | Cox | 128/421 |
| 4,459,977 | 7/1984 | Pizon et al. | 600/16 |
| 4,666,443 | 5/1987 | Portner | 600/16 |
| 4,759,760 | 7/1988 | Snapp, Jr. | 623/3 |
| 4,804,358 | 2/1989 | Karcher et al. | 600/17 |
| 4,813,952 | 3/1989 | Khalafalla | 600/17 |
| 4,995,857 | 2/1991 | Arnold | 600/16 |

FOREIGN PATENT DOCUMENTS 0269254 6/1988 European Pat. Off. .

OTHER PUBLICATIONS

Acker et al, "Journal of Thoracic & Cardiovascular Surgery" vol. 94, No. 2, Aug. 1987, pp. 163-174.
Biomechanical Cardiac Assist Cardiomyoplasty and Muscle Powered Devices; Ray C.-J. Chiu; Futura Publishing Co., Inc.; Mount Kisko, New York 1986; pp. 141-150, FIG. 8, p. 149 "Skeletal Muscle-Powered Cardiac Assist Using an Extra-Aortic Balloon Pump" by J. R. Neilson and R. C.-J. Chiu.
Transformed Muscle for Cardiac Assist and Repair; Ray C.-J. Chiu and Ivan Bourgeois; Futura Publishing Co.; Inc.; Mount Kisko, New York, 1990; pp. 321-327, FIG. 1C p. 325.
Figure 1d p. 326; "Skeletal Muscle-Powered Counter Pulsater", by C. Desrosiers; et al.
Cardiomyoplasty; Carpenteir, et al; Futura Publishing Co., Inc.; Mount Kisko, New York 1991; pp. 227-249, FIG. 1 p. 229, FIG. 10 p. 239; "Skeletal Muscle-Powered Counter Pulsation" by Bridges, et al.
The American Journal of Cardiology, vol. 41, Jun. 1978, pp. 1191 through 1201; Farcot, Jean C; Meerbaun. Samuel; Lang, Tzu-Wang; Kaplan-Leo, Corday, Eliot.

Primary Examiner—William E. Kamm
Attorney, Agent, or Firm—Reed A. Duthler; Robert J. Klepinski; Harold R. Patton

[57] ABSTRACT

An implantable coronary perfusion assist system to divert blood from large arteries, such as the aorta, to small arteries, such as the coronary arteries where additional blood flow is needed. The assist system includes a shunt graft which is connected to the aorta or another convenient source of oxygenated blood at one end, and to the coronary artery or the atrium at its other end. A pump, preferably of the type employing a trained muscle wrapped around a fluid chamber is connected by a conduit to a bladder disposed in line with the graft, to assist in pumping of blood from the aorta to the coronary artery. The pump action is synchronized to the dastolic phase of the patient's cardiac cycle, and the coronary perfusion is accomplished without increasing the concentration of oxygen in the patient's body.

12 Claims, 1 Drawing Sheet

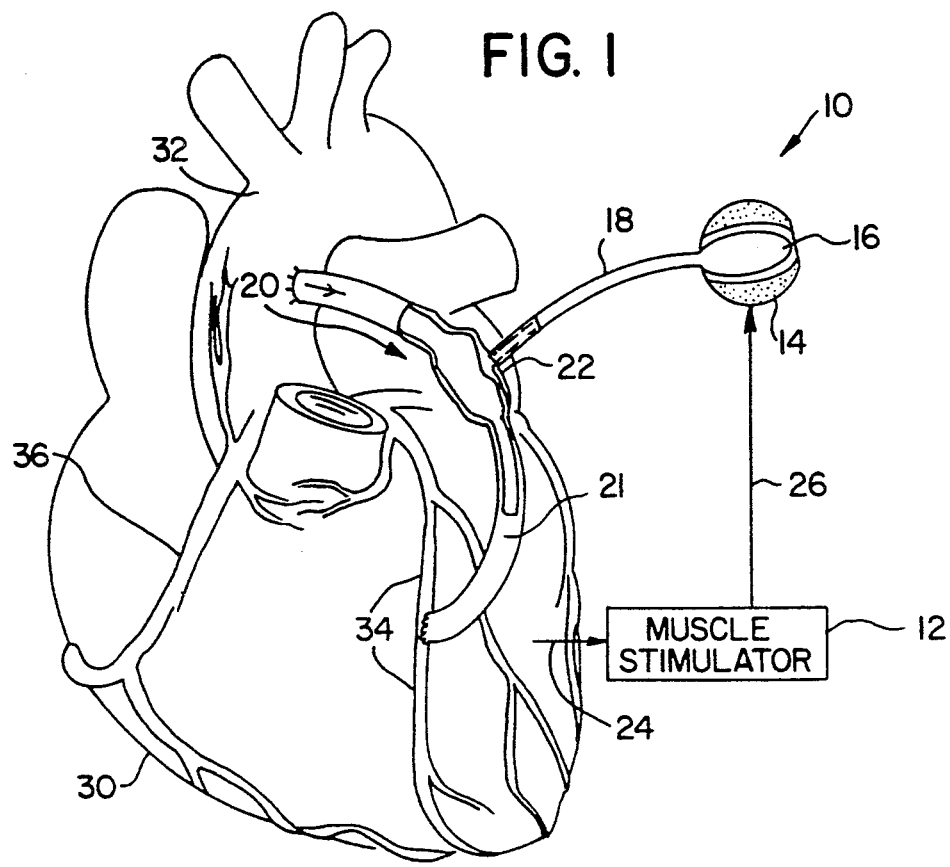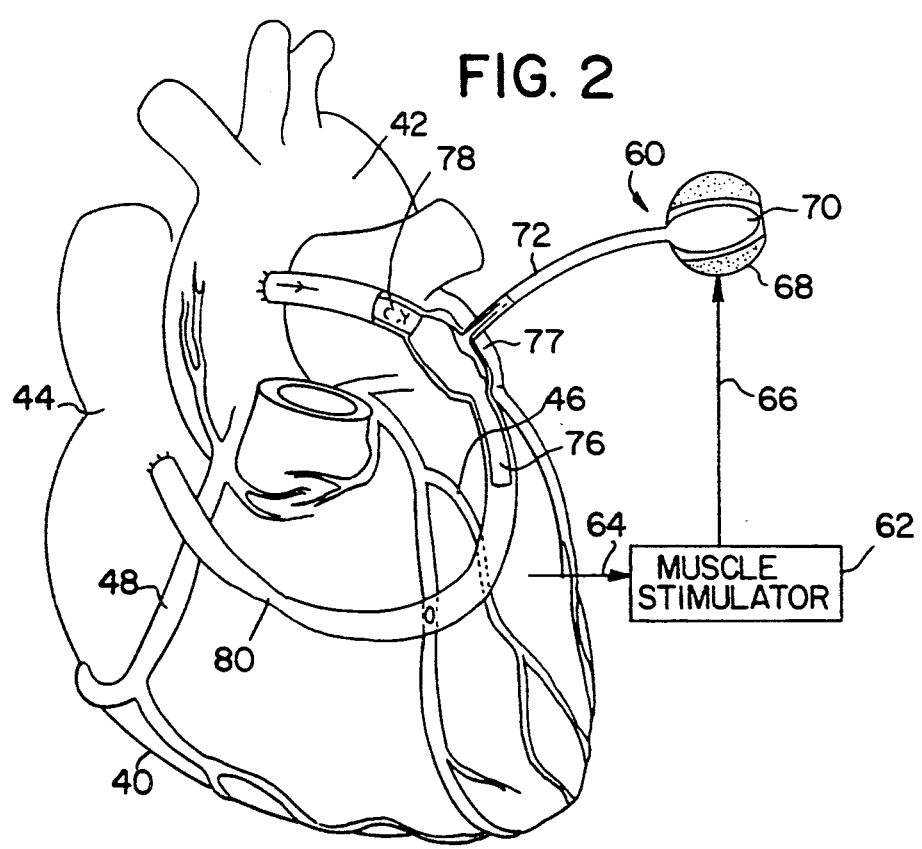

IMPLANTABLE SYSTEM AND METHOD FOR CORONARY PERFUSIONS ASSISTANCE

FIELD OF THE INVENTION

This invention relates to devices for increasing blood flow to small arteries.

BACKGROUND OF THE INVENTION

The partial or total blockage of small arteries, such as the coronary arteries providing blood to the heart, may result in ischemia and permanent tissue damage. Many therapies are used to improve coronary blood flow. For example, intraaortic balloon pumps (IABP) are used, in part, to augment coronary circulation by the principle of counter-pulsation. These are commonly used for up to 72 hours.

Where more permanent solution is required to the blockage of the specific arteries, surgery can be performed to put in place a "bypass" to move blood around the occluded artery portion. One very commonly used procedure of this type is the coronary artery bypass.

Other methods are used for opening the occlusion, such as balloon angioplasty which uses an inflatable member to expand a blocked area. Another family of devices breaks up and removes the stenosis blocking the artery. This is commonly known as atherectomy. This is performed by mechanical means as well as lasers.

In cases where the coronary artery disease is more wide spread, it is difficult to treat the disease with these prior art methods. The more diffuse the disease, the more difficult it is to use the existing therapies.

It is well known in the art to use trained skeletal muscle as an implantable pump. For example, see U.S. Pat. No. 4,411,268 to Cox which discloses muscle training methods. Such muscle pumps are well known in the area of cardiac assist for improving blood flow in the aorta as taught by Ray C.J. Chiu, M.D. in his book "Biomechanical Cardiac Assist".

The concept of providing flow from the aorta to coronary arteries by a bypass is known. A side-by-side anastomosis of this type shunt to the various arteries is demonstrated in the prior art. These attempts have not, however, recognized the need for a pump to assist in providing blood to these coronary arteries.

What is needed is a therapy that can provide blood flow through the coronary arteries generally so as to treat diffuse coronary artery problems and which has a capability, when desired, to provide assisted blood flow to the heart, especially during diastole, when the heart muscle around the diseased arteries is relaxed.

SUMMARY OF THE INVENTION

The present invention is a coronary perfusion assist system and method to move blood from large arteries, such as the aorta, to small arteries where additional blood flow is needed. The preferred embodiment includes a shunt from the aorta or other convenient source of oxygenated blood to the coronary artery which is supplemented by a pump. The pump is preferably of the type employing a trained muscle wrap around a fluid chamber. The pump action is synchronized to the diastolic phase of the patient's cardiac cycle, and coronary perfusion is accomplished without increasing the concentration of oxygen in the patient's body.

In one embodiment, a bladder pump is installed around the shunt with a fluid path leading to a sac inside the trained muscle. A muscle stimulator is attached to the heart for sensing heartbeats to synchronize the device. When assist of the coronaries is desired, the muscle stimulator will stimulate the trained muscle which will squeeze the fluid in the reservoir which in turn will increase pressure in the bladder to pump on the shunt.

In other embodiments, the shunt can further be directed into the right atrium to use the atrium as a compliance chamber to avoid over pressure. The shunt may also preferably include a flow control element with or without a valve to prevent backflow in the shunt itself.

BRIEF DESCRIPTION OF THE DRAWINGS

FIG. 1 is a schematic view of a heart employing the pump of the present invention.

FIG. 2 is an alternative embodiment of the device of FIG. 1 showing use of a valve, a flow control element, and a compliance chamber.

DETAILED DESCRIPTION OF THE PREFERRED EMBODIMENT

As illustrated in FIG. 1, the device 10 includes a muscle stimulator 12, muscle wrap 14, fluid reservoir 16, fluid transmission tube 18, pump 20 including bladder pump 22 and shunt 21. Muscle stimulator 12 is of the type commonly used in prior art cardiac assist devices. Stimulator 12 is connected by line 24 to the heart so that stimulator 12 is capable of sensing heartbeats. Stimulator 12 is connected by line 26 to muscle 14 so that stimulator 12 can electronically stimulate muscle 14 for contraction.

Apparatus 10 is shown connected to heart 30 on which is illustrated aorta 32 and coronary arteries including the Left Anterior Descending Artery (LAD) 34, and the Right Coronary Artery (RCA) 36.

In this embodiment, shunt (graft) 21 is connected to provide blood from aorta 32 to artery 34 in a manner generally known in the prior art. In this invention, however, pump 20 is in line in shunt 21 to assist in the transfer of blood.

The programming physician selects the parameters of assist, choosing to stimulate muscle 14 preferably when the heart is in diastole. As is known in the prior art, one need not provide assist with each beat of the heart. The number of beats per assist can be varied. The ratio of beats to an assist is programmed in stimulator 12. Muscle stimulator 12 will stimulate tissue 14 at the programmed ratio. Tissue 14 will contract squeezing reservoir 16 and increasing pressure in line 18 into bladder 22. Bladder 22 will contract squeezing shunt 21. This will cause blood to flow from shunt 21 into coronary artery 34 bathing the heart tissue with oxygenated blood.

This system augments the coronary artery circulation in a manner much more effectively than the prior art. Prior art cardiac assist devices only affect the coronary arteries remotely indirectly since they assist circulation throughout the whole body. The entire compliance capacity of the peripheral circulation system must be overcome in order to benefit the coronary arteries. This coronary pump of the present invention perfuses the coronary arteries directly.

In the present invention, much smaller quantities of blood need to be moved in order to significantly help the coronary arteries. For example, the common coronary flow is approximately 300ml per minute. In one mode where the present invention moves only 1ml of blood per cardiac cycle, this would result in 60ml per minute. This is a 20% increase in blood flow to the coronary arteries. Obviously, this is a great increase compared to the relatively small effort by the pump. Since small amounts of blood need be transported, smaller muscle wraps can be employed than are required for the large aorta systems. An additional part of this invention is that times when the pump is not activated there is a natural flow through shunt 21 so there is always a flow of blood, even in times when there is no pump cycling.

The embodiment of FIG. 2 shows additional features which augment the present invention. This illustration shows heart 40 having an aorta 42, right atrium 44, LAD 46 and RCA 48. Device 60 is shown to include stimulator 62, sensing line 64, stimulation line 66, muscle wrap 68, reservoir 70, fluid tube 72, shunt 76, valve 78, and flow control element 80. Pump 70 generally operates in the manner shown in the previous embodiment. In this embodiment. However, shunt 76 is directed into right atrium 44. Right atrium 44 acts as a compliance chamber to prevent over pressure and keep the system regulated.

Flow control element 80 is used to control pressure. One example of a flow control device which is appropriate would be a Possis Perma-Flow graft.

In the illustrated embodiment, shunt 76 is attached to artery 46 by side-by-side anastomosis in a manner known in the prior art. In other embodiments, shunt 76 is attached by side anastomosis to other arteries, such as artery 48.

This embodiment further preferably includes valve 78 in shunt 76 which prevents backflow. For example, a valved conduit constructed in the manner of the Medtronic Hall aortic valved conduit prosthesis may be utilized. Thus, all pumping pressure will force blood down into the coronary arteries and prevent flow back into the aorta.

This device bathes multiple coronary arteries in blood from the aorta while expending a minimum amount of energy in the pumping process. The tissue which most needs the blood for survival of the patient, the coronary tissue, receives the required blood in the most efficient manner possible. This reduces the need for large muscle wraps.

What is claimed is:

1. A coronary perfusion assist system, for pumping blood from a large artery to a coronary artery in synchrony with a diastolic phase of a patient's cardiac cycle comprising:
   a. implantable shunt means having a proximal end and a distal end, for diverting arterial blood from a body source to a coronary artery;
   b. connecting means for joining said proximal end to the large artery and for joining said distal end to the coronary artery, in order to divert arterial blood from the large artery to the coronary artery;
   c. implantable pump means, coupled to said shunt means, for assisting the flow of the arterial blood in said shunt means wherein said pump means includes:
      a bladder pump connected intermediate said proximal and distal ends of said shunt means for controlling the flow of arterial blood through said shunt means;
      a fluid chamber;
      a fluid conduit connected intermediate said fluid chamber and said bladder pump; and
      a muscle wrapped around said fluid chamber, wherein said fluid conduit transmits a force applied by the muscle on said fluid chamber to said bladder pump.
   d. synchronizing means for activating said pump means in response to the diastolic phase of the cardiac cycle.

2. The assist system as defined in claim 1, wherein the synchronizing means comprises:
   a. means for sensing a diastolic phase of a cardiac cycle;
   b. means, responsive to said sensing means, for generating control signals in response to the diastolic phase of the cardiac cycle; and
   c. control means, coupled to said pump means, for activating said pump means in response to said control signals.

3. The assist system as defined in claim 2, wherein said pump means further includes a muscle stimulator for stimulating the muscle at predetermined intervals.

4. The assist system as defined in claim 1, wherein said shunt means includes an arterial graft.

5. A coronary perfusion assist system, for pumping blood from a large artery to a coronary artery in synchrony with a diastolic phase of a patient's cardiac cycle comprising:
   a. implantable shunt means having a proximal end and a distal end;
   b. connecting means for joining a coronary artery intermediate said proximal end and said distal end of said shunt means, and for joining said proximal end to a large artery and for joining said distal end to a cardiac atrium, for diverting arterial blood from the large artery partially past said coronary artery to the atrium;
   c. implantable pump means, coupled to said shunt means, for assisting the flow of the arterial blood in said shunt means; and
   d. synchronizing means for activating said pump means in response to the diastolic phase of the cardiac cycle, 6. The coronary perfusion assist system as defined in claim 5, wherein said pump means includes:
   a. a bladder pump connected intermediate said proximal and distal ends of said shunt means for controlling the flow of arterial blood through said shunt means;
   b. a fluid chamber;
   c. a fluid conduit connected intermediate said fluid chamber and said bladder pump; and
   d. a muscle wrapped around said fluid chamber, wherein said fluid conduit transmits a force applied by the muscle on said fluid chamber to said bladder pump.

7. The coronary perfusion assist system as defined in claim 5, wherein the synchronizing means comprises:
   a. means for sensing a diastolic phase of a cardiac cycle;
   b. means, responsive to said sensing means, for generating control signals in response to the diastolic phase of the cardiac cycle; and
   c. control means, coupled to said pump means, for activating said pump means in response to said control signals.

8. The coronary perfusion assist system as defined in claim 5, further comprising:
   means for preventing backflow of oxygenated blood from said coronary artery to said large artery.

9. The coronary perfusion assist system as defined in claim 8, wherein said backflow prevention means includes a one-way valve.

10. The coronary perfusion assist system as defined in claim 5, wherein said shunt means includes an arterial graft.

11. Method for coronary perfusion assistance comprising the steps of:
   a. implanting an arterial shunt having a proximal end and a distal end, wherein said shunt further comprises a pump for selectively assisting flow of blood through the shunt;
   b. disposing said arterial shunt along a path external to the cardiac tissue, large artery and coronary artery;
   c. connecting said proximal end to a large artery and said distal end to a coronary artery, for diverting arterial blood from the large artery to the coronary artery; and
   d. energizing the pump in synchrony with a diastolic phase of a patient's cardiac cycle.

12. The method as defined in claim 11, said energizing step further including the steps of:
   a. sensing cardiac activities;
   b. generating control signals in response to the sensed cardiac activities; and
   c. selectively activating said pump in response to said control signals.

* * * * *